United States Patent
Karge et al.

(10) Patent No.: US 12,377,428 B2
(45) Date of Patent: Aug. 5, 2025

(54) METHOD FOR EVALUATING A PUMP ACTUATION, AND FLUID DISPENSER AND EVALUATION UNIT WHICH USE THIS METHOD

(71) Applicant: Aptar Radolfzell GmbH, Radolfzell (DE)

(72) Inventors: Marius Karge, Stockach (DE); Kevin Schmid, Constance (DE)

(73) Assignee: Aptar Radolfzell GmbH, Radolfzell (DE)

( * ) Notice: Subject to any disclaimer, the term of this patent is extended or adjusted under 35 U.S.C. 154(b) by 458 days.

(21) Appl. No.: 17/907,581

(22) PCT Filed: Apr. 8, 2021

(86) PCT No.: PCT/EP2021/059233
§ 371 (c)(1),
(2) Date: Sep. 28, 2022

(87) PCT Pub. No.: WO2021/209320
PCT Pub. Date: Oct. 21, 2021

(65) Prior Publication Data
US 2023/0129079 A1     Apr. 27, 2023

(30) Foreign Application Priority Data
Apr. 14, 2020  (EP) .................................. 20169402

(51) Int. Cl.
*B05B 12/00*     (2018.01)
*B05B 11/10*     (2023.01)
*B05B 11/00*     (2023.01)

(52) U.S. Cl.
CPC ........ *B05B 12/004* (2013.01); *B05B 11/1029* (2023.01); *B05B 11/1052* (2023.01); *B05B 11/0038* (2018.08)

(58) Field of Classification Search
CPC .............. B05B 12/004; B05B 11/1029; B05B 11/1052; B05B 11/0038; B05B 11/108; G16H 20/10; G16H 40/63; G16H 40/67
See application file for complete search history.

(56) References Cited

U.S. PATENT DOCUMENTS

| | | |
|---|---|---|
| 9,168,551 B2 | 10/2015 | Heisel et al. |
| 10,406,304 B2 | 9/2019 | Koerner |

(Continued)

FOREIGN PATENT DOCUMENTS

| | | |
|---|---|---|
| CN | 107750178 A | 3/2018 |
| CN | 110831704 A | 2/2020 |

(Continued)

OTHER PUBLICATIONS

Office Action issued in corresponding Chinese Patent Application No. 202180029051.5, with English translation, dated Aug. 12, 2023 (20 pages).

(Continued)

*Primary Examiner* — Ishal Pancholi
(74) *Attorney, Agent, or Firm* — FLYNN THIEL, P.C.

(57) ABSTRACT

A method for evaluating the pump actuation for a pump dispenser that includes two sub-units which can be moved manually towards one another and a pump which has a pump chamber that can be made smaller by moving the sub-units from a first end position into an actuated second end position. The force with which the sub-units are moved towards one another is detected by a force sensor during movement of the sub-units. The curve over time of the detected force is evaluated such that an increase in force is identified which is characteristic for reaching the actuated second end position. Depending on whether the increase in force was detected, a signal which is characteristic for the result is haptically, acoustically and/or visually output and/

(Continued)

or transmitted via a wireless interface to an external display apparatus, by means of an output device.

19 Claims, 6 Drawing Sheets

(56) References Cited

U.S. PATENT DOCUMENTS

| | | |
|---|---|---|
| 11,179,739 B2 | 11/2021 | Baumann |
| 11,369,761 B2 | 6/2022 | Tritschler et al. |
| 2007/0272764 A1 | 11/2007 | Poulard |
| 2014/0243749 A1 | 8/2014 | Edwards et al. |
| 2017/0065777 A1 | 3/2017 | Koerner |
| 2021/0106777 A1 | 4/2021 | Decock et al. |
| 2021/0354157 A1 | 11/2021 | Graham et al. |

FOREIGN PATENT DOCUMENTS

| | | |
|---|---|---|
| DE | 102011079950 B3 | 11/2012 |
| DE | 102014204939 B3 | 12/2014 |
| EP | 3636348 A1 | 4/2020 |
| FR | 2861460 A1 | 4/2005 |
| FR | 3077496 A1 | 8/2019 |
| WO | 2014/106096 A1 | 7/2014 |

OTHER PUBLICATIONS

International Search Report, with English translation, issued in corresponding International Application No. PCT/EP2021/059233, date of mailing Jul. 5, 2021 (6 pages).
Written Opinion of International Searching Authority, issued in corresponding International Application No. PCT/EP2021/059233, date of mailing Jul. 5, 2021 (10 pages).

METHOD FOR EVALUATING A PUMP ACTUATION, AND FLUID DISPENSER AND EVALUATION UNIT WHICH USE THIS METHOD

The invention relates to the field of pump dispensers for discharging fluid, in particular pump dispensers in the medical field, which are filled with a pharmaceutical fluid. In such pump dispensers, it is provided that by manual actuation of a pump of the pump dispenser, fluid can be discharged from a fluid reservoir through a discharge opening, for example in the form of an atomized spray, an unatomized jet, or in the form of individual drops.

Pump dispensers are used by users to apply pharmaceutical fluids, for example by nasal or oral route and in particular also sublingually, i.e., under the tongue. Particularly in the case of pharmaceutical fluids with an unpleasant taste or odor, there is a risk that the user will not perform a complete discharge, but instead will terminate the actuation too early. The result is an insufficient amount of pharmaceutical fluid discharged.

PROBLEM AND SOLUTION

The problem addressed by the invention is to provide a method and devices for carrying out the method which reduces or prevents the risk of incomplete discharge.

According to the invention, a method for evaluating a pump actuation on a pump dispenser for discharging a fluid, in particular a pharmaceutical fluid, is proposed for this purpose, which is used when a pump dispenser is used which has two sub-units, which can be moved manually relative to one another, and which has a pump having a pump chamber that can be made smaller by moving the sub-units from an unactuated first end position into an actuated second end position. The preferably pharmaceutical fluid passes from the fluid reservoir, which is preferably between 20 ml and 1000 ml in size, to the pump and from there on to a discharge opening. The fluid stored in the fluid reservoir can be, in particular, a pharmaceutical, in particular containing pharmaceutically active substances, but in particular allergen extracts.

The two sub-units, which may in particular be a base with a fluid reservoir on the one hand and an actuating unit with an actuating pusher and a discharge opening on the other hand, are pressed towards one another in the course of the discharge, wherein the pump is actuated by pressing the sub-units together. Many pump dispensers are designed for one-handed operation by grasping the fluid reservoir with the hand and pressing down an actuating pusher with one finger of the hand, usually the index finger.

The discharge opening can be provided in particular laterally on the actuating unit so that a discharge direction forms an angle >0° with the actuating direction of the actuating unit, preferably between 60° and 120°. For a better approach of the discharge opening towards the application site, a design in which a freely projecting applicator tube is provided, at the distal end of which the discharge opening is arranged, can be advantageous.

In particular, the actuating unit can also be provided for the sublingual applicator. In this case, an angled applicator tube tip is preferably provided at the end of the applicator tube projecting laterally from the actuating unit.

The pump can be, in particular, a piston pump, which is designed as a piston pump with a pump cylinder and a pump piston displaceable therein. The pump cylinder and pump piston jointly delimit the pump chamber, wherein pressure-dependent opening and closing valves are preferably provided on the inlet side and outlet side of the pump chamber. When the sub-units are moved towards one another, the inlet valve closes, the outlet valve opens, and the movement of the pump piston in the pump cylinder associated with the movement of the sub-units displaces fluid, which is conveyed through the outlet valve to the discharge opening and is discharged therefrom. On the return stroke, the outlet valve closes, the inlet valve opens, and fluid is drawn from the fluid reservoir into the pump chamber.

In addition to piston pumps, however, other types of pumps can also be used, which, for the purpose of pumping in one direction, can be pressurized to an end position and which return to a starting position on the return stroke. These pumps include, for example, bellows pumps.

To detect the actuated second end position, in accordance with the invention, the force with which the sub-units are manually moved towards one another is detected by a force sensor during the movement of the sub-units towards one another. This force is the force applied by the user, in particular between their hand grasping one sub-unit and the finger, in particular the index finger, pressing down on the other sub-unit.

A force sensor in the sense of the invention is a sensor that returns the applied force in the form of an analog force value, i.e., a value that is higher corresponding to the higher the force applied by the user. Accordingly, a simple switch is not a force sensor in the sense of the invention. However, sensors which return a measured value directly traceable to the applied force are also force sensors in the sense of the invention, so in particular also a pressure sensor or a displacement sensor coupled to a resetting spring force.

The force sensor can preferably be an FSR sensor (Force Sensitive Resistor) or a piezo sensor. These sensors provide analog sensor values in the form of variable resistances or voltages.

The force sensor is preferably assigned a resetting spring force, which, when the actuating force ceases, presses the surfaces of the evaluation unit acting on the force sensor back into an initial position. In particular, the force sensor is preferably decoupled from one of the surfaces acting on the force sensor in the initial position due to the spring force, for example by a narrow gap, so that the force sensor reliably supplies a zero signal in this initial position.

According to the invention, the force sensor values reported by the force sensor are evaluated in such a way that a force increase characteristic of reaching the actuated second end position is detected. The way in which this can be achieved will be explained later. The result of the evaluation is that it is recognized whether the characteristic force increase in question was detected, which results from the fact that the pump has reached its end position, in particular that the pump piston has moved into the pump cylinder to its lowest end position. It has been shown that the reaching of this end position by the user unintentionally leads to actuation with a stronger and identifiable actuating force.

Depending on whether the force increase characteristic of reaching the actuated second end position has been detected, a signal characteristic of the result is preferably then output haptically, acoustically and/or visually by an output device. The output preferably takes place on the pump dispenser itself or on an evaluation unit attached to the pump dispenser. A haptic signal is, for example, a vibration signal. A visual signal can be generated in particular by a display or an LED, wherein different signals with different colors or flashing sequences can be distinguished if necessary. An acoustic signal can in particular consist of one or more different signal tones.

In the simplest case, a signal is output as positive feedback when the characteristic course of the force for reaching the second actuated stroke end position has been detected. This could be, for example, a green illumination of an LED or a vibration. Alternatively or additionally, it can be provided that a signal is output as negative feedback if no characteristic progression of the force for the second actuated stroke end position is detected after detection of the start of discharge, wherein the trigger for this signal can be the expiry of a predefined time period from the start of actuation. Alternatively, a drop in the force sensor value can be detected as a discontinuation of the actuation force. An LED could indicate the negative result, for example, by lighting up red.

Furthermore, it is also possible to output a signal during actuation to indicate to the user that the start of actuation has been detected, in particular when the force sensor value has exceeded a predetermined minimum. Such a signal ends as soon as the force increase characteristic of reaching the actuated second end position is detected and/or as soon as the termination of the actuation is detected, and a positive or a negative feedback is output as a signal accordingly.

Signaling, in particular direct signaling at the pump dispenser or at an evaluation unit attached thereto, is regarded as the preferred use of the result of the evaluation. However, it may instead or preferably additionally be provided that the result of the evaluation is sent to an external display device via a wireless interface. The wireless interface may be one of the common interfaces such as WLAN, Bluetooth, NFC, 3G, 4G or 5G, wherein Bluetooth 4.x or 5.x is preferred. The external display device is preferably a cell phone or a smart watch.

The external display device can reproduce the result of the evaluation according to the display described above. The external display device can also store the results and/or pass them on to external servers for evaluation by third parties. The results can also be used by a training program, with which the correct use of the pump dispenser is made clear to the user.

In the simplest case, the evaluation for identifying the reaching of the actuated second end position can be performed by a processor evaluating the current force value without taking into account the previously detected force values. For example, exceeding a previously defined threshold value can be interpreted as an indication of the force increase when the second end position is reached. However, such an approach is problematic because it is difficult to find an absolute threshold value that occurs equally for fast and slow actuation.

It is therefore advantageous if the data detected by the force sensor are stored in a memory in such a way that the course of the detected force over time results from this. For example, the force sensor could be interrogated at a frequency of 500 Hz from the detection of the start of actuation and the force values stored in a memory. This results in the course of the force value over time.

The evaluation used to determine whether a force increase characteristic of reaching the actuated second end position has occurred is therefore preferably performed taking this course over time into account. Such an evaluation allows a higher reliability in the distinction of reaching or not reaching the second end position.

The evaluation of the course of the detected force over time is preferably performed in such a way that the slope of the corresponding graph is used to detect the second end position. In particular, the slope of the force over time can be evaluated. Here, an increase in the slope, i.e., the first derivative of the force over time, can be interpreted as an indicator for reaching the second end position. In particular, a quotient can be formed from the slope, i.e., the force increase over a defined period of time, and the force value. This indicates the slope relative to the previously reached force level. This quotient can be compared with a limit value and exceeding this limit value can be interpreted as reaching the second end position. The corresponding limit value can be determined by tests. In particular, the limit value is also not constant, but variable over time, namely, is descending. Thus, in the simplest case, the limit value can decrease linearly. It is also possible to reset the limit value depending on whether predefined force values are reached.

The evaluation of the force over time is preferably performed using a smoothed graph of the force over time. This eliminates high frequencies in the manner of a low-pass filter. Such frequencies can result in particular from friction on surfaces of the pump dispenser that slide along one another.

The evaluation of the force over time can also be performed in such a way that the force detected by the force sensor is used to categorize the actuation into one of at least two categories that are assigned to actuations of different strengths and/or speeds. In particular, this categorization can take place in a short first period of the actuation, for example within the first 0.5 seconds or less. The categorization allows the identification of whether the second actuated end position has been reached and, if so, when this occurred, to be performed in different ways for the at least two categories. These different ways can be reflected in different limit values used for the analysis. However, the evaluation can also be fundamentally different. For example, a comparatively high actuating force at a very early stage can lead to an analysis in which the reaching of the second end position is assumed to be given, since the user can no longer prevent the end position from being reached in practice anyway. Only the corresponding time is then determined, wherein other rules can be used to determine this than for slow or normal actuation.

It is considered disadvantageous if the evaluation unit for evaluating the actuating force has to be switched on before actuation by the user. Preferably, the corresponding evaluation unit is always active instead. In order to nevertheless achieve a low power requirement, it is considered advantageous if the evaluation is performed using a processor which has a normal operating mode as well as a power-saving sleep mode. Until the pump dispenser is actuated, the processor is in sleep mode. In the sleep mode, the processor monitors whether the force value of the force sensor exceeds a predefined limit value, in particular predefined by a voltage or resistance level. Parts of the processor not required for this monitoring can be switched off in the meantime. If the limit value is exceeded, the processor switches to operating mode.

In this operating mode, which is then reached, the values detected by the force sensor are digitized by an A/D converter and stored in the memory and then analyzed, preferably repeatedly, by the processor to identify whether the force increase characteristic of reaching the actuated second end position can be detected. The operating mode has a considerably higher energy requirement than the sleep mode. However, due to the only short stay in the operating mode, the higher energy requirement is not very significant. As soon as a discharge process has been completed, either after the second actuated end position has been reached or after the second actuated end position has not been reached and after the associated signaling, the processor can switch back to the sleep mode.

In addition to the force sensor described, other sensors can be provided in the evaluation unit used to carry out the method, in particular position sensors or acceleration sensors. The sensor values of the other sensors can be used as a supplement in the method described above, for example to identify an upcoming use of the pump dispenser and/or to monitor whether an intended shaking of the pump dispenser has taken place properly. Sensor values of these sensors or values derived therefrom can be used to influence output signals of the dispensing device and/or can be forwarded wirelessly to a display device.

In addition to the method described above, the invention also relates to systems in which the described method is used.

In particular, the invention also relates to a pump dispenser for discharging a fluid, in particular for discharging a pharmaceutical fluid. Such a pump dispenser has a fluid reservoir for receiving the fluid prior to discharge and at least one discharge opening through which fluid can be discharged into an environment. The pump dispenser further has an actuating pusher, which is displaceable relative to the fluid reservoir, and a pump having a pump chamber, wherein walls of the pump chamber are movable relative to one another between an unactuated first end position and an actuated second end position for the purpose of reducing the size of the pump chamber, and wherein a first wall of the pump chamber is provided stationary relative to the fluid reservoir and a second wall of the pump chamber is displaceable relative to the first wall by manual actuation of the actuating pusher. In particular, the walls of the pump chamber may be walls formed by a pump cylinder and a pump piston of the pump. The walls of the pump chamber can also be opposite walls of a bellows pump.

In addition, the pump dispenser has an evaluation unit for identifying when the second actuated end position has been reached and for using this identification in the method described. For this purpose, the evaluation unit has electronic components which are preferably powered by a battery. The pump dispenser also includes a force sensor as explained above, which measures the force applied by a user between the actuating pusher and the second wall, for example the pump piston, or between a retaining surface on the fluid reservoir and the first wall, for example the pump cylinder. The evaluation unit further has a processor, which evaluates the force detected by the force sensor so that a force increase characteristic of reaching the actuated second end position can be detected. In addition, the evaluation unit preferably has an output device, which, depending on the force evaluation, outputs a signal characteristic of the result of the force evaluation as a haptic, acoustic and/or visual signal. In particular, the output device can be a vibration device or an LED. In addition, or, if necessary, also as an alternative to the output device, the evaluation unit has a wireless interface, which, as a function of the force evaluation, can send a signal characteristic of the result of the force evaluation to an external display device in order to allow the signal to be used or forwarded in the sense described above.

The evaluation unit described can be permanently integrated in the pump dispenser so that the evaluation unit cannot be separated from components thereof, in particular from the pump, without the use of tools. This can be useful for dispensers with exchangeable or refillable fluid reservoirs.

However, it is preferred to use an evaluation unit for a pump dispenser for discharging a fluid, in particular for discharging a pharmaceutical fluid, which is also included by the invention and which is provided for tool-free attachment to a pump dispenser. In this case, the corresponding pump dispenser comprises the fluid reservoir for receiving the fluid prior to discharge, the at least one discharge opening through which fluid can be discharged into an environment, and an actuating pusher which is displaceable relative to the fluid reservoir, as well as the pump which is actuatable by displacement of the actuating pusher relative to the fluid reservoir between an unactuated first end position and an actuated second end position.

The evaluation unit, which can be attached to this embodiment of the pump dispenser without the use of tools, is designed to identify when the second actuated end position has been reached by use of the method described above. The evaluation unit is preferably attached to the pump dispenser via a clamping or snap-action mechanism. The attachment is preferably performed in such a way that the force sensor of the evaluation unit is arranged between an actuating surface of the evaluation unit and an actuating surface on the pump dispenser which is replaced thereby with regard to handling and is only indirectly actuated.

In a first preferred design, the evaluation unit is designed to be attached to the fluid reservoir and has a fastening region for stationary contact with the fluid reservoir or a coupling surface stationary for this purpose, as well as a retaining surface for manual gripping of the evaluation unit. The evaluation unit further has the described force sensor, which in this case detects the force applied by a user between the retaining surface and the fastening region. Accordingly, in such a design, it is envisaged that the user no longer grips around the fluid reservoir itself in the region of the retaining surface in order to press the two sub-units of the pump dispenser towards one another, but instead grips the retaining surface of the evaluation unit. If the other sub-unit of the pump dispenser, in particular the actuating unit with actuating pusher, is now pressed down, this force also acts between the retaining surface of the evaluation unit and the fastening region and can be detected there by the force sensor. The fastening region is the portion of the evaluation unit which is in direct contact with the fluid reservoir or a surface fixed thereto and which is capable of exerting a force acting in the direction of the other sub-unit on the sub-unit of the fluid reservoir. In particularly preferred embodiments, the fastening region is not only a contact surface for applying force to the fluid reservoir, but a retaining device that is coupled to the fluid reservoir sub-unit in such a way that the fluid reservoir is held thereon sufficiently firmly that the fluid reservoir does not separate from the fastening region even in an overhead position.

In particular, an evaluation unit designed to be attached to the fluid reservoir preferably has a housing with a casing wall into which the fluid reservoir of the pump dispenser can be inserted and the outer side of which forms the retaining surface. The fastening region of the evaluation unit is preferably provided here inside the casing wall and comes into contact there with the inserted pump dispenser.

The fastening region is preferably provided with at least one elastically deflectable retaining element and is designed to receive the pump dispenser in such a way that, when the pump dispenser is inserted into the fastening region, the at least one retaining element is elastically deflected to thereby produce a retaining force. In particular, the fastening region can be formed by a fastening cup that has a plurality of elastically deflectable retaining elements circumferentially distributed, for example in the form of inwardly pointing ribs on a circumferential ring wall of the fastening cup.

In an alternative second design, the evaluation unit is provided on the other sub-unit. The evaluation unit is thus designed to be attached to the actuating pusher or the actuating pusher sub-unit and has a fastening region for stationary contact with the actuating pusher and an actuating surface for manually pressing down the evaluation unit. As with the first embodiment presented, fastening is achieved here preferably by a clamping or snap-action connection. The evaluation unit also has a force sensor in the sense described above, which in this case detects the force applied by a user between the actuating surface and the fastening region. In this alternative design, it is envisaged that the user no longer directly depresses the actuating pusher provided on the pump dispenser in order to press the two sub-units of the pump dispenser towards one another, but instead depresses the actuating surface of the evaluation unit. If the actuating surface is now pressed down against the other part unit of the pump dispenser, this force also acts between the actuating surface of the evaluation unit on the one hand and the actuating pusher of the pump dispenser and the fastening region adjacent thereto on the other hand and can be detected there by the force sensor.

Irrespective of whether the evaluation unit is attached to the fluid reservoir or to the actuating unit, the evaluation unit has a processor, which evaluates the force detected by the force sensor so that a force increase characteristic of reaching the actuated second end position is detected, and the evaluation unit has an output device, which, as a function of the force evaluation, outputs a signal characteristic of the result of the force evaluation as a haptic, acoustic and/or visual signal and/or via a wireless interface, which, as a function of the force evaluation, can send a signal characteristic of the result of the force evaluation to an external display device.

An evaluation unit for tool-free attachment allows the unit to be easily coupled to and decoupled from a pump dispenser when the fluid reservoir is emptied and the evaluation unit is to be attached to a new pump dispenser.

The evaluation unit which can be attached without the use of tools is intended to be used together with a pump dispenser and can also be offered as part of a set consisting of a pump dispenser and an evaluation unit.

BRIEF DESCRIPTION OF THE DRAWINGS

Further advantages and aspects of the invention will become apparent from the claims and from the following description of preferred exemplary embodiments of the invention, which are explained below with reference to the figures.

DETAILED DESCRIPTION OF THE EXEMPLARY EMBODIMENTS

Figures 1A, 1B:
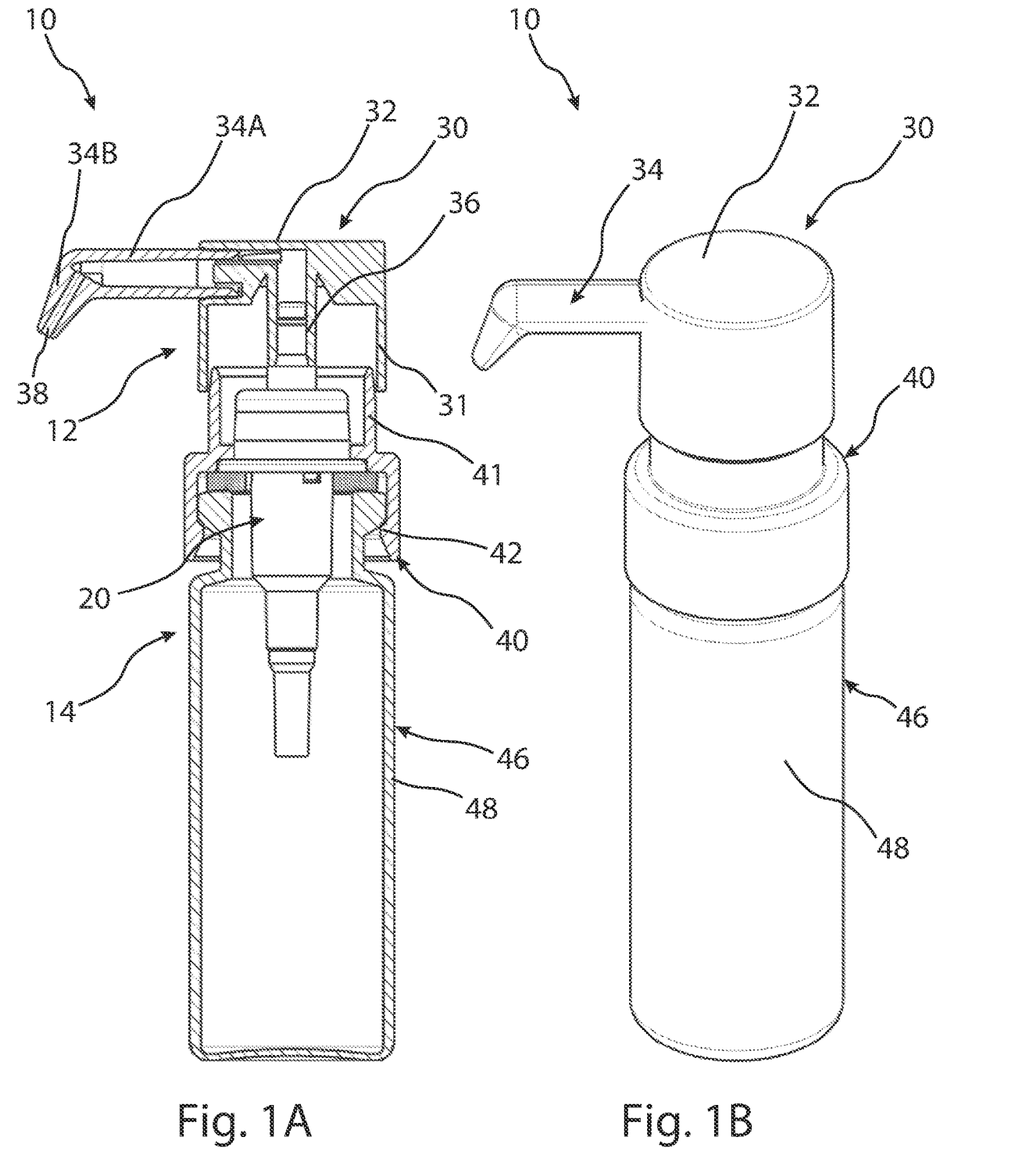
FIGS. 1A and 1B show a pump dispenser, which in the present example is designed as a pump dispenser for sublingual application of a pharmaceutical fluid.

FIGS. 1A and 1B show a pump dispenser 10. The pump dispenser 10 comprises a fluid reservoir 46 in which a pharmaceutical fluid is stored prior to discharge. For the discharge of the fluid, the pump dispenser 10 has a pump 20 and a discharge opening 38. With regard to the intended discharge of fluid under the tongue of the user, the discharge opening 38 is provided in the illustrated pump dispenser 10 at the distal end of a laterally freely projecting applicator tube 34, which in the specific embodiment has a radial tube portion 34A and an applicator tube tip 34B bending downwards therefrom.

The discharge opening 38 is provided on an actuating unit 30, which can be pressed down in a vertical direction relative to the fluid reservoir 46 and a base 40 connected thereto, wherein the actuating unit 30 is guided by a sliding ring 31 sliding on a sliding surface 41 of the base 40. Pressing down is performed as intended by the user grasping the fluid reservoir 46 with their hand in the region of the retaining surface 48 and/or the base 40 and by applying downward force to the actuating unit 30 at its actuating pusher 32 with their index finger. The downward force actuates a pump 20, the pump cylinder of which is clamped between the bottle body of the fluid reservoir 46 and the base 40, while a piston unit projecting upwardly from the pump cylinder with a pump outlet channel is inserted in a clamping manner into a discharge channel 36 of the actuating unit. By pressing down the actuating unit 30 relative to the fluid reservoir 46, the piston unit is pressed into the pump cylinder and the fluid contained in the pump chamber is conveyed to the discharge opening. The intended discharge volume is achieved only when the actuating unit 30 is pressed into a mechanically predetermined end position.

Figure 2:
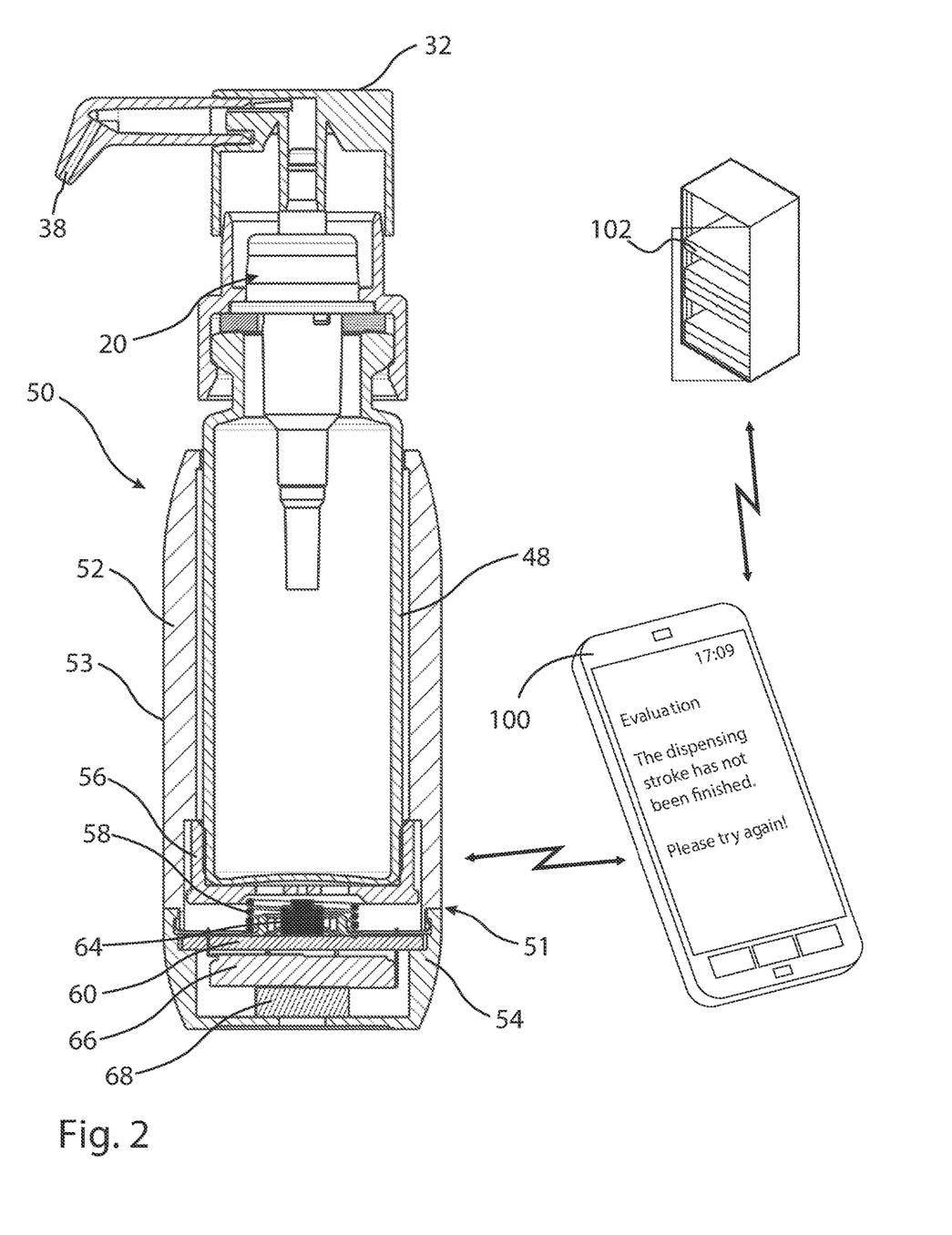
FIG. 2 shows the dispenser of FIGS. 1A and 1B supplemented by an evaluation unit coupled without the use of tools.
Figure 3:
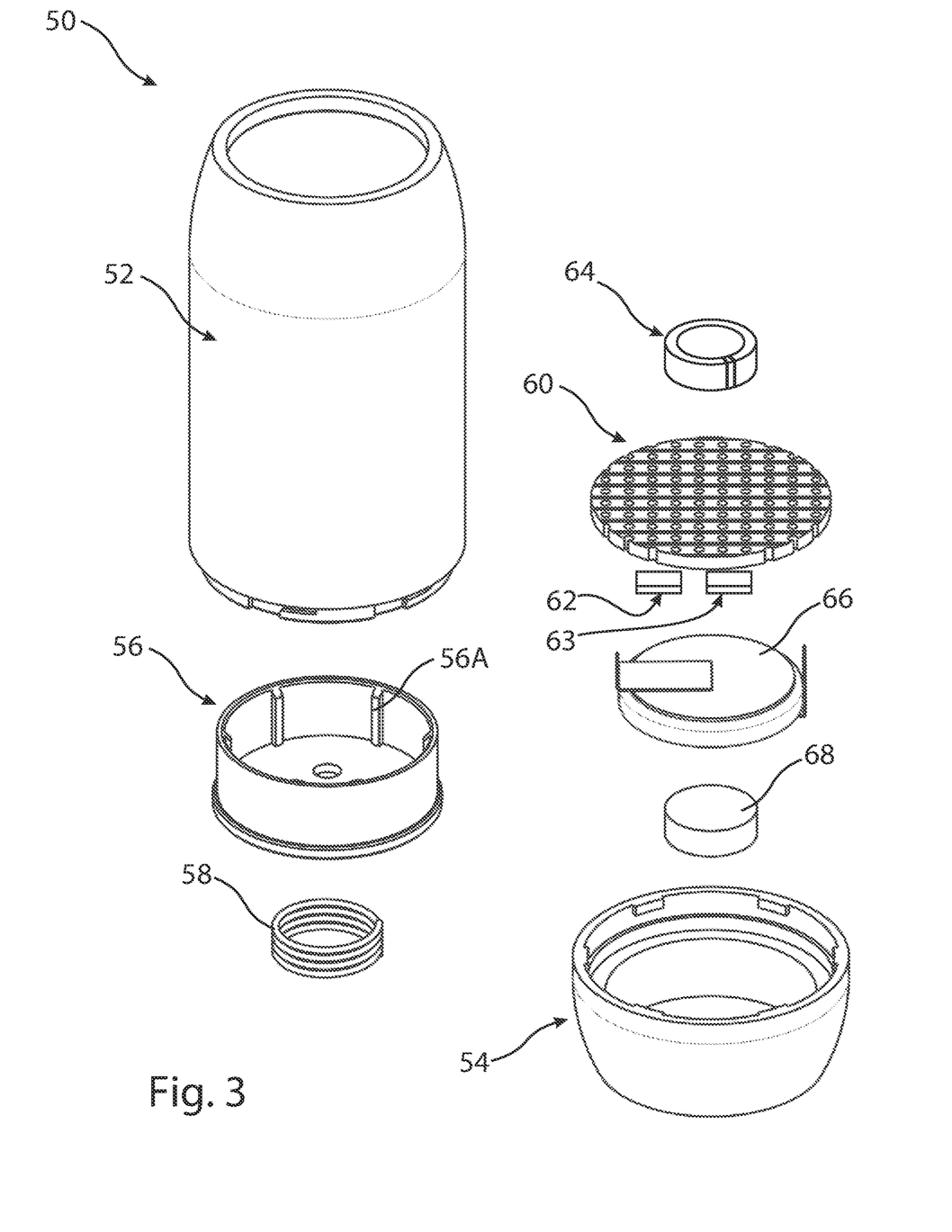
FIG. 3 shows the individual components of the evaluation unit of FIG. 2.

To monitor the downward force, the evaluation unit 50 is provided, which is shown in sectional view in FIG. 2 and the individual components of which can be taken from the exploded view in FIG. 3. The evaluation unit comprises a housing formed from two components 52, 54, wherein the component 54 forms a base and the component 52 forms a casing wall which surrounds a receiving space. The receiving space is delimited at a lower end thereof by a cup-like component forming a fastening region 56, into which the fluid reservoir 46 is inserted to form a clamping connection. Internal ribs 56A of the component are deflected outwardly when the fluid reservoir 46 is inserted, thereby causing a clamping stress. A circuit board 60 is provided below the cup-like component, with a force sensor 64 in the manner of an FSR sensor being provided on the upper side of the circuit board. The force sensor is surrounded by a compression spring 58, which, in the fully relaxed state, lifts the cup-like component in such a way that cup-like component loses contact with the force sensor 64. A processor 62 and a radio module 63 are provided on an underside of the circuit board 60 for communication with a cell phone 100 and indirectly with a server 102. Furthermore, a battery 66 and a vibration signal generator 68 are connected to contacts on the underside of the circuit board 60.

The pump dispenser 10 supplemented by the evaluation unit 50 can be operated by the user in an almost unchanged manner. However, the user's hand no longer directly grips the retaining surface 48 of the fluid reservoir 46, but the retaining surface 53 of the evaluation unit 50. If the user then presses the actuating pusher 32, the corresponding force also acts on the force sensor 64, taking into account the spring force of the spring 58, so that the corresponding force sensor values are available to the processor 62.

Figure 4A:
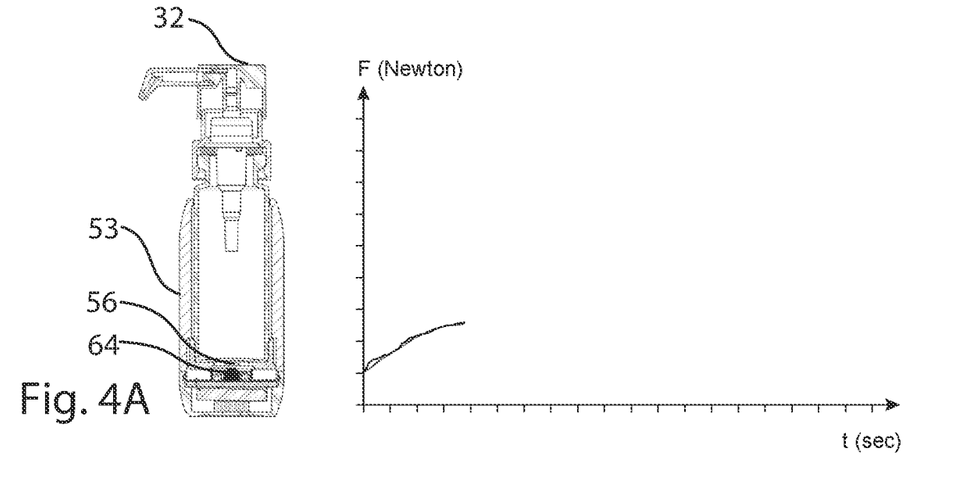
FIGS. 4A to 4C illustrate the use of the pump dispenser with the evaluation unit attached.
Figure 4B:
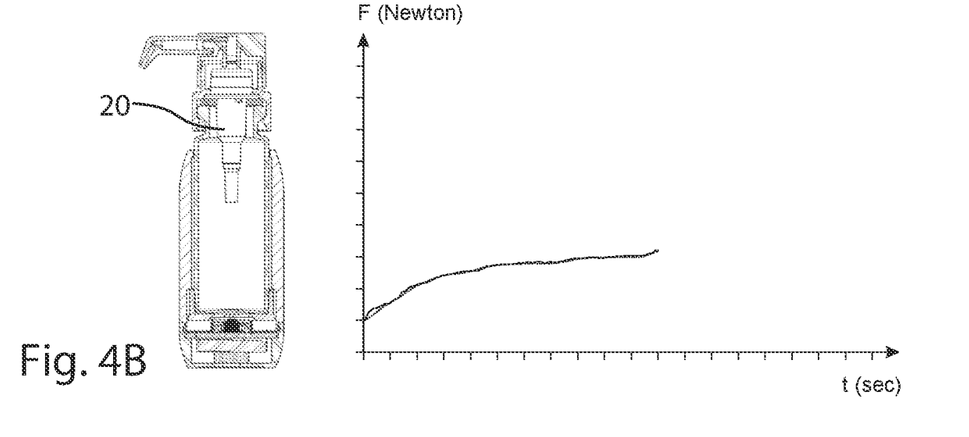
Figure 4C:
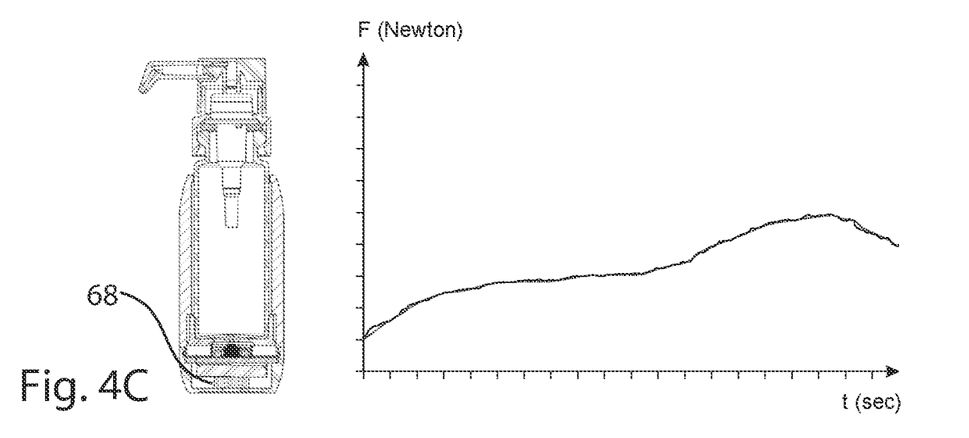

FIGS. 4A to 4C show how the force is detected during actuation.

Prior to use, the processor 62 is in a low-power mode, in which the processor 62 remains until the first time the force sensor value of the force sensor 64 exceeds zero. This occurs as soon as, upon actuation, the spring 58 is compressed to the point where the force sensor 64 is contacted by the mounting portion 56 and force is applied by the mounting portion 56.

At this time, the processor 62 changes to an operating mode and stores the force sensor values of the force sensor 64 in the operating mode at a predetermined frequency, for example 500 Hz. The corresponding values are stored in the memory of the evaluation unit 50 from this point on. The graphs shown on the right in FIGS. 4A to 4C illustrate this by the solid line in each case.

In a first actuation phase, towards the end of which the state of FIG. 4A is reached, the force sensor value increases. This is the phase before discharge, in which the gaps between individual components of the pump dispenser and also to the evaluation unit are initially compressed. Towards the end of this first actuation phase, the fluid is discharged.

FIG. 4B illustrates that the actuation force increases only slightly during fluid discharge. This increase is primarily due to the increasingly tensioned spring of the pump 20. FIG. 4B shows the pump dispenser 10 at the end of the fluid discharge phase. The pump piston has now reached an end position defined by the geometry of the pump chamber.

FIG. 4C illustrates that a further force increase now follows, while the relative position of the sub-units of the pump dispenser changes only slightly. This is due to the deformability of the components, but no longer leads to fluid discharge. The user can notice the end of the fluid discharge as well as the increasing force.

In particular, however, the user notices a vibration generated by the vibration signal generator 68 because the processor 62 has detected that the second actuated stroke end position has been reached based on the course shown in FIGS. 4A to 4C.

Figure 5A:
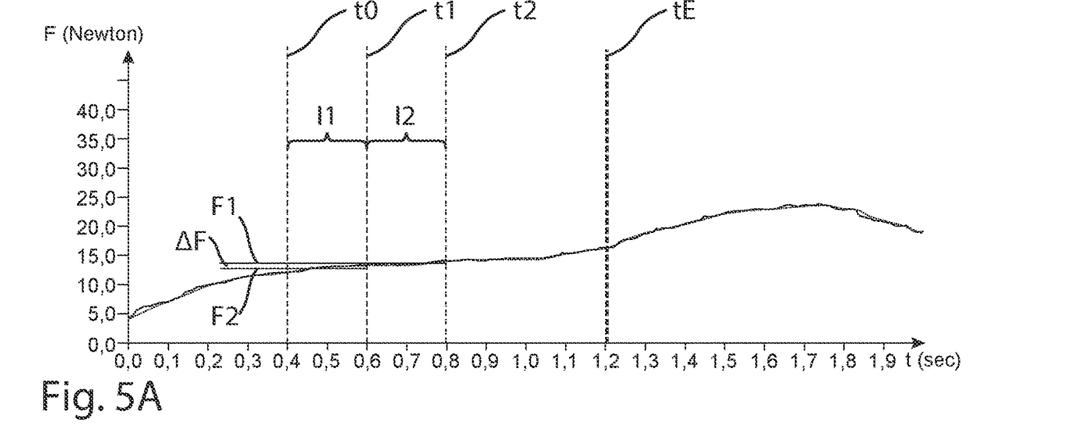
FIGS. 5A to 5C show force-time courses for different types of actuation.
Figure 5B:
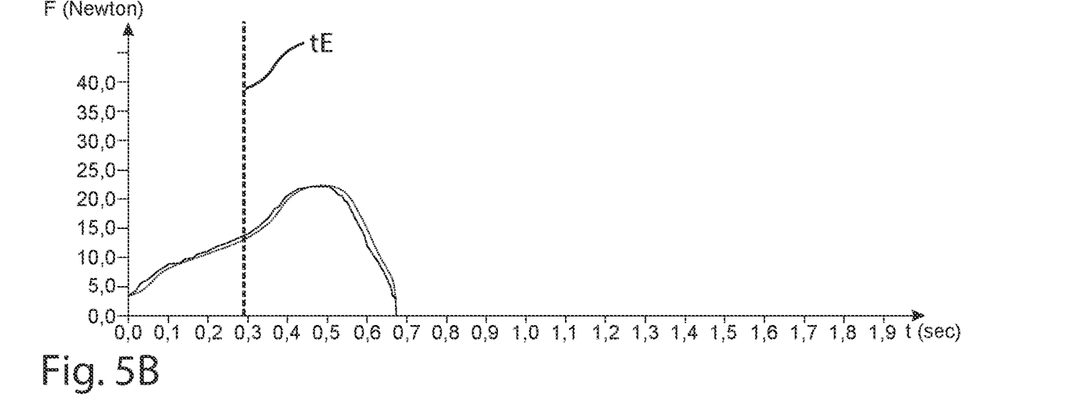
Figure 5C:
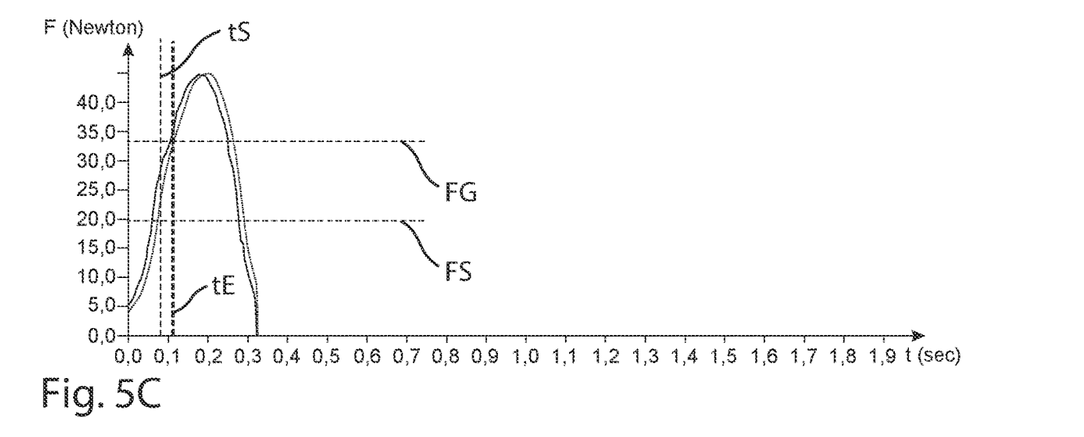

With reference to FIGS. 5A to 5C, it will be explained how the evaluation can be performed by the processor 62. Here, FIG. 5A shows the force-time course corresponding to FIGS. 4A to 4C. The graphs of FIGS. 5B and 5C each show actuations with varying degrees of force.

The evaluation is performed as follows:

FIG. 5A, similarly to FIGS. 4A to 4C, shows the force-time course determined by the force sensor with a solid line. By use of the processor 62, the force-time course is smoothed, for example by the moving average method. The correspondingly smoothed course is illustrated in the figures with a dotted line.

The smoothed course is used primarily for further analysis. One possible method is for the processor to use the smoothed measured values already available in such a way that at a current time $t2$, the processor examines for time points in the past, by way of example here for time $t1$, in each case a time interval $I1$ lying back from this time and a time interval $I2$ lying in the future. For both intervals of defined time length, a mean force value is determined, the values being referred to as $F1$ and $F2$ in FIG. 5A. The difference of the mean force values is referred to as $\Delta F$ in FIG. 5A. On the basis of the force difference $\Delta F$ and one of the two values $F1$ and $F2$ or their sum, a quotient is formed, for example $\Delta F/F1$, which indicates, as it were, how strongly the course of the measured values in the interval $I2$ increases in relation to the previous interval $I1$.

This quotient, in the present case by way of example $\Delta F/F1$, is compared with a limit value. The limit value is usually a time-variable limit value which, starting from the beginning of the manual force application, decreases over time, in the simplest case linearly. If the quotient is above the limit value, this is interpreted as reaching the second actuated end position. In the case of the actuation of FIG. 5A, the limit value is exceeded at time tE. As an alternative to a decrease over time, the limit value can also be adjusted in steps when an associated force value is reached in each case.

The described method allows the correct interpretation of the force course as they result from slow and normal actuation according to FIGS. 5A and 5B.

However, it has been shown that very powerful actuations, as shown in FIG. 5C, cannot always be analyzed very well with this method, since here the force does not increase over time after reaching the actuated end position to the same extent as with normal or slow actuation.

The described method is therefore supplemented by the following approach: if an immediate clear increase in the measured force is detected after the start of actuation, for example a reaching or exceeding of a predefined force value FS within a short time period tS, or if an early strong slope of the graph is determined by another type of calculation, this is an indicator of a very forceful and/or fast actuation. With such an actuation, the reaching of the second end position by the user can no longer be prevented in practice. Thus, it becomes clear already within the short time period tS that the second end position is properly reached. In this case, the time of reaching the second actuated end position is no longer determined on the basis of an evaluation of the gradient as described above, but on the basis of reaching a limit force FG which is above the force value FS. If the measured force value exceeds this limit force FG, this is a sufficiently accurate indicator that the second end position has been reached.

Figure 6:
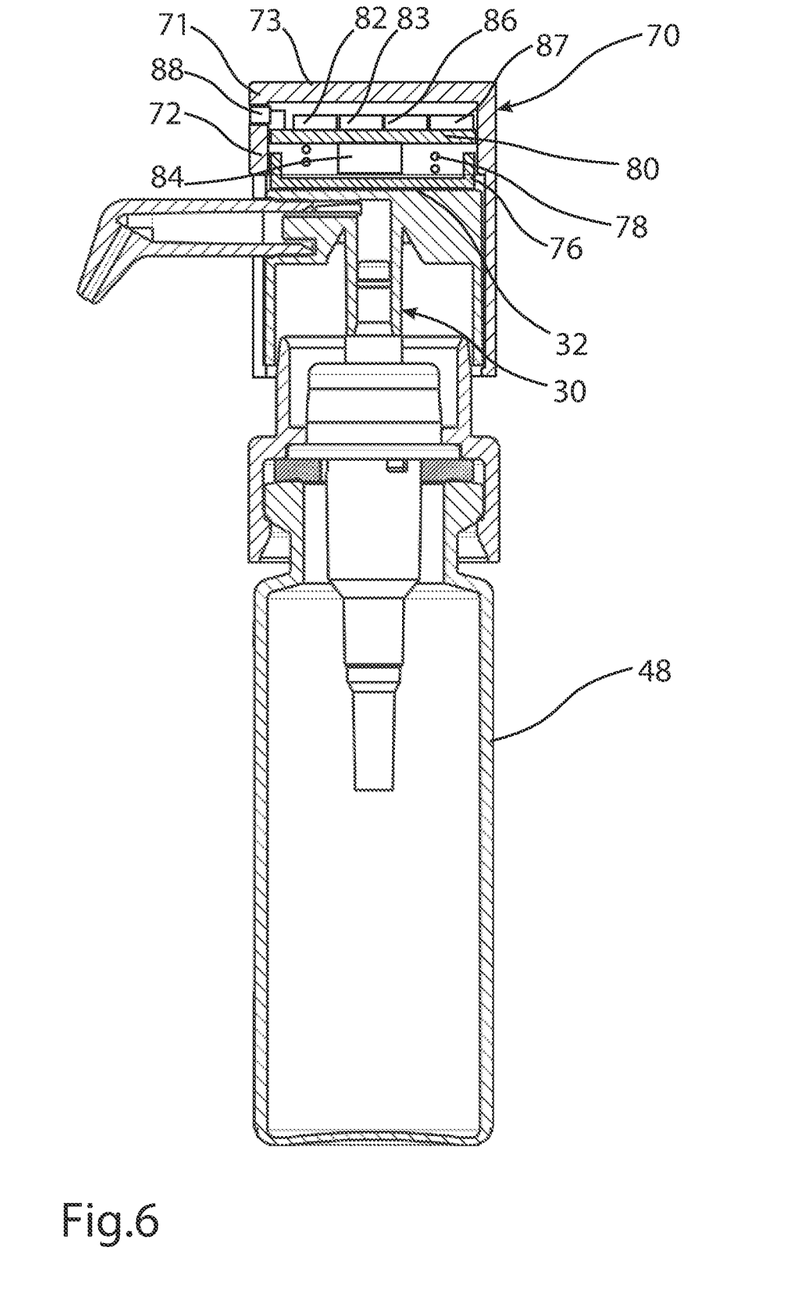
FIG. 6 shows an alternative embodiment of an evaluation unit attached to the pump dispenser of FIGS. 1A and 1B.

FIG. 6 illustrates in schematic form an alternative design of an evaluation unit 70. The evaluation unit 70 is intended to be placed on the actuating unit 30 and the actuating pusher 32 there. It comprises similar components to the embodiment of the evaluation unit 50 described above, but includes a housing 71 which has an upper actuating surface 73 instead of the retaining surface 53. The housing 71 has a lateral surface which has a recess in the region of the applicator tube 34. At the lower end of the lateral surface, a detent cam is provided for coupling to the actuating unit 30, in this case to the sliding ring 31. Within the housing 71, the fastening region 76 is provided for stationary contact with the actuating pusher 32. Furthermore, similarly to the embodiment of the evaluation unit 50 described above, a circuit board 80 is provided, equipped with a force sensor 84, a microprocessor 82, a radio module 83 and a battery 86. An LED 88 is provided as an output device instead of the vibration signal generator 68. By way of example for both evaluation units 50, 70, the evaluation unit 70 further comprises a position and acceleration sensor 87, by which the vertical orientation of the dispenser during actuation and/or the proper shaking before actuation can be detected.

The force sensor 84 detects the actuation force in the same way as the previously described force sensor 64. In principle, therefore, an identical force-time course is also produced, as illustrated in FIGS. 4A to 4C and 5A to 5C. Deviating from the description in this regard, the present embodiment preferably provides that the start of the actuation and thus of the evaluation begins a signal, for example by the LED radiating yellow. If the second actuated end position of the pump 20 is then not detected, for example for 1 second, the color changes to red. If, on the other hand, the second actuated end position is reached and thus a complete proper discharge is detected, the color changes to green.

The invention claimed is:

1. A method for evaluating a pump actuation on a pump dispenser for discharging a fluid comprising:
   providing the pump dispenser with two sub-units, which can be moved manually relative to one another, and a pump having a pump chamber that can be made smaller by moving the sub-units from an unactuated first end position into an actuated second end position;
   detecting the actuated second end position, wherein a force with which the sub-units are manually moved towards one another is detected by a force sensor during movement of the sub-units towards one another;
   wherein a course of the detected force over time is evaluated in such a way that a force increase characteristic of reaching the actuated second end position is identified; and
   depending on whether the force increase characteristic of reaching the actuated second end position has been detected, at least one of the following:
   outputting a signal characteristic of a result haptically;
   outputting the signal characteristic of the result acoustically;
   outputting the signal characteristic of the result visually; and
   sending the signal characteristic of the result via a wireless interface to an external display device by an output device; and
   storing data detected by the force sensor in a memory in such a way that the course of the detected force over time is determined;
   wherein an evaluation used to determine whether the force increase characteristic of reaching the actuated second end position has occurred is performed taking the course of the detected force over time into account.

2. The method as claimed in claim 1, wherein:
   the evaluation is performed using a processor which has an operating mode as well as a power-saving sleep mode;
   the force sensor is connected to the processor in such a way that the processor in the sleep mode switches into the operating mode once a predetermined limit value is exceeded; and
   subsequently, in the operating mode, values detected by the force sensor are stored in the memory and repeatedly analyzed by the processor to identify the force increase characteristic of reaching the actuated second end position.

3. A method for evaluating a pump actuation on a pump dispenser for discharging a fluid comprising:
   providing the pump dispenser with two sub-units, which can be moved manually relative to one another, and a pump having a pump chamber that can be made smaller by moving the sub-units from an unactuated first end position into an actuated second end position;
   detecting the actuated second end position, wherein a force with which the sub-units are manually moved towards one another is detected by a force sensor during movement of the sub-units towards one another;
   wherein a course of the detected force over time is evaluated in such a way that a force increase characteristic of reaching the actuated second end position is identified; and
   depending on whether the force increase characteristic of reaching the actuated second end position has been detected, at least one of the following:
   outputting a signal characteristic of a result haptically;
   outputting the signal characteristic of the result acoustically;
   outputting the signal characteristic of the result visually; and
   sending the signal characteristic of the result via a wireless interface to an external display device by an output device;
   the method further including at least one of the following:
   the evaluation of the force over time is performed using a smoothed graph of the force over time;
   the evaluation of the force over time is performed in such a way that a slope of the force over time is evaluated, wherein an increase in the slope is interpreted as an indicator for reaching the actuated second end position; and
   the evaluation of the force over time is performed in such a way that the force detected by the force sensor is used to categorize the actuation into one of at least two categories that are assigned to actuations of at least one of different strengths and different speeds, wherein the reaching of the actuated second end position, the time of reaching the actuated second end position, or both the reaching of the actuated second end position and the time of reaching the actuated second end position are identified in different ways for the at least two categories.

4. A method for evaluating a pump actuation on a pump dispenser for discharging a fluid comprising:
   providing the pump dispenser with two sub-units, which can be moved manually relative to one another, and a pump having a pump chamber that can be made smaller by moving the sub-units from an unactuated first end position into an actuated second end position;
   detecting the actuated second end position, wherein a force with which the sub-units are manually moved towards one another is detected by a force sensor during movement of the sub-units towards one another;
   wherein a course of the detected force over time is evaluated in such a way that a force increase characteristic of reaching the actuated second end position is identified; and
   depending on whether the force increase characteristic of reaching the actuated second end position has been detected, at least one of the following:
   outputting a signal characteristic of a result haptically;
   outputting the signal characteristic of the result acoustically;
   outputting the signal characteristic of the result visually; and
   sending the signal characteristic of the result via a wireless interface to an external display device by an output device;
   the method including at least one of the following:
   the outputting or sending of the signal characteristic is performed in such a way that after a start of the actuation a first signal is output, which ends as soon as the force increase characteristic of reaching the actuated second end position is detected, as soon as a course of the force over time or a force value characteristic of an end of the actuation has been measured, or both as soon as the force increase characteristic of reaching the actuated second end position is detected and as soon as the course of the force over time or the force value characteristic of the end of the actuation has been measured;

the outputting or sending of the signal characteristic is performed in such a way that a second signal is output when the force increase characteristic of reaching the actuated second end position has been detected; and the outputting or sending of the signal characteristic is performed in such a way that a third signal is output as soon as a course of the force over time or the force value characteristic of the end of actuation has been measured.

5. The method as claimed in claim 1, wherein:
at least one of measurement data and data for detecting the force increase, detected by the force sensor, are sent to an external display device via a wireless interface.

6. A pump dispenser for discharging a fluid comprising:
a fluid reservoir for receiving the fluid prior to discharge and at least one discharge opening through which the fluid can be discharged into an environment;
an actuating pusher which is displaceable relative to the fluid reservoir;
a pump having a pump chamber, wherein walls of the pump chamber are movable relative to one another between an unactuated first end position and an actuated second end position for reducing a size of the pump chamber, and wherein a first wall of the walls of the pump chamber is provided stationary relative to the fluid reservoir and a second wall of the walls of the pump chamber is displaceable relative to the first wall by manual actuation of the actuating pusher; and
an evaluation unit for identifying when the actuated second end position has been reached;
the evaluation unit having a force sensor which measures a force applied by a user between the actuating pusher and the second wall or between a retaining surface on the fluid reservoir and the first wall;
the evaluation unit having a processor which evaluates the force detected by the force sensor so that a force increase characteristic of reaching the actuated second end position is detected; and
at least one of the following:
(a) the evaluation unit having an output device which, depending on a force evaluation, at least one of the following:
outputs a signal characteristic of a result of the force evaluation as a haptic signal;
outputs the signal characteristic of the result of the force evaluation as an acoustic signal; and
outputs the signal characteristic of the result of the force evaluation as a visual signal; and
(b) the evaluation unit having a wireless interface, which, as a function of the force evaluation, can send the signal characteristic of the result of the force evaluation to an external display device.

7. An evaluation unit system for a pump dispenser for discharging a fluid comprising:
an evaluation unit configured for tool-free attachment to the pump dispenser which has a fluid reservoir for receiving the fluid prior to discharge, at least one discharge opening through which the fluid can be discharged into an environment, and an actuating pusher, wherein the pump dispenser further has a pump which is actuatable by displacement of the actuating pusher relative to the fluid reservoir between an unactuated first end position and an actuated second end position;
the evaluation unit being designed to identify when the actuated second end position has been reached;
the evaluation unit being:
designed to be attached to the fluid reservoir and having a fastening region for stationary contact with the fluid reservoir and a retaining surface for manual gripping of the evaluation unit, wherein the evaluation unit further has a force sensor for detecting the force applied by a user between the retaining surface and the fastening region, or designed to be attached to the actuating pusher and having a fastening region for stationary contact with the actuating pusher and an actuating surface for manually pressing down the evaluation unit, wherein the evaluation unit further has a force sensor which detects a force applied by a user between the actuating surface and the fastening region;
the evaluation unit having a processor which evaluates the force detected by the force sensor so that a force increase characteristic of reaching the actuated second end position is identified; and
at least one of the following:
(a) the evaluation unit having an output device, which, as a function of a force evaluation, at least one of the following:
outputs a signal characteristic of a result of the force evaluation as a signal;
outputs the signal characteristic of the result of the force evaluation as an acoustic signal; and
outputs the signal characteristic of the result of the force evaluation as a visual signal; and
(b) the evaluation unit having a wireless interface, which, as the function of the force evaluation, can send the signal characteristic of the result of the force evaluation to an external display device.

8. The evaluation unit system as claimed in claim 7, wherein:
the evaluation unit is designed to be attached to the fluid reservoir;
the evaluation unit has a housing with a casing wall into which the fluid reservoir of the pump dispenser can be inserted and an outside of which forms the retaining surface; and
the fastening region of the evaluation unit is provided inside the casing wall and is configured to come into contact there with the inserted pump dispenser.

9. An evaluation unit system for a pump dispenser for discharging a fluid comprising:
an evaluation unit configured for tool-free attachment to the pump dispenser which has a fluid reservoir for receiving the fluid prior to discharge, at least one discharge opening through which the fluid can be discharged into an environment, and an actuating pusher, wherein the pump dispenser further has a pump which is actuatable by displacement of the actuating pusher relative to the fluid reservoir between an unactuated first end position and an actuated second end position;
the evaluation unit being designed to identify when the actuated second end position has been reached;
the evaluation unit being:
designed to be attached to the fluid reservoir and having a fastening region for stationary contact with the fluid reservoir and a retaining surface for manual gripping of the evaluation unit, wherein the evaluation unit further has a force sensor for detecting the force applied by a user between the retaining surface and the fastening region, or designed to be attached to the actuating pusher and having a fastening region for stationary contact with the actuating pusher and an actuating surface for manually pressing down the evaluation unit, wherein the evaluation unit further has a force sensor which detects a force applied by a user between the actuating surface and the fastening region;

the evaluation unit having a processor which evaluates the force detected by the force sensor so that a force increase characteristic of reaching the actuated second end position is identified; and at least one of the following:
(a) the evaluation unit having an output device, which, as a function of a force evaluation, at least one of the following:
  outputs a signal characteristic of a result of the force evaluation as a signal;
  outputs the signal characteristic of the result of the force evaluation as an acoustic signal; and
  outputs the signal characteristic of the result of the force evaluation as a visual signal; and
(b) the evaluation unit having a wireless interface, which, as the function of the force evaluation, can send the signal characteristic of the result of the force evaluation to an external display device;

wherein the evaluation unit is designed to be attached to the fluid reservoir;

wherein the evaluation unit has a housing with a casing wall into which the fluid reservoir of the pump dispenser can be inserted and an outside of which forms the retaining surface;

wherein the fastening region of the evaluation unit is provided inside the casing wall and is configured to come into contact there with the inserted pump dispenser; and wherein the fastening region is provided with at least one elastically deflectable retaining element and is designed to receive the pump dispenser in such a way that, when the pump dispenser is inserted into the fastening region, the retaining element is elastically deflected and thereby produces a retaining force.

10. A set comprising a pump dispenser and the evaluation unit system as claimed in claim 7;
wherein the pump dispenser has a fluid reservoir and an actuating pusher movable relative to the fluid reservoir; and
wherein the evaluation unit is attached to the fluid reservoir or to the actuating pusher of the pump dispenser.

11. The pump dispenser as claimed in claim 6, wherein:
the pump dispenser has an actuating unit which comprises the actuating pusher and the discharge opening and which as a whole is displaceable in an actuation direction relative to the fluid reservoir for actuating the pump.

12. The pump dispenser as claimed in claim 6, including at least one of the following:
the fluid reservoir is filled with a pharmaceutical fluid;
the fluid reservoir has a volume between 20 ml and 1000 ml; and
the pump is designed as a piston pump with a pump cylinder and a pump piston displaceable therein, which together delimit the pump chamber.

13. The pump dispenser as claimed in claim 6, including at least one of the following:
the force sensor is designed as an FSR sensor (Force Sensitive Resistor) or as a piezo sensor;
a spring is associated with the force sensor and spaces the components acting on the force sensor from one another in such a way that one of the components loses contact with the force sensor;
the evaluation unit comprises at least one further sensor;
the evaluation unit comprises an energy source in the form of a battery; and
the evaluation unit comprises a radio interface.

14. The pump dispenser as claimed in claim 11, including at least one of the following:
the discharge opening is provided laterally on the actuating unit so that a discharge direction forms an angle >0° with the actuation direction; and
the actuating unit has an applicator tube, at a distal end of which the discharge opening is provided.

15. The set as claimed in claim 10, wherein:
the pump dispenser has an actuating unit which comprises the actuating pusher and the discharge opening and which as a whole is displaceable in an actuation direction relative to the fluid reservoir for actuating the pump.

16. The set as claimed in claim 15, including at least one of the following:
the discharge opening is provided laterally on the actuating unit so that a discharge direction forms an angle >0° with the actuation direction; and
the actuating unit has an applicator tube, at a distal end of which the discharge opening is provided.

17. The set as claimed in claim 10, including at least one of the following:
the fluid reservoir is filled with a pharmaceutical fluid;
the fluid reservoir has a volume between 20 ml and 1000 ml; and
the pump is designed as a piston pump with a pump cylinder and a pump piston displaceable therein, which together delimit a pump chamber.

18. The evaluation unit as claimed in claim 7, including at least one of the following:
the force sensor is designed as an FSR sensor (Force Sensitive Resistor) or as a piezo sensor;
a spring is associated with the force sensor and spaces components acting on the force sensor from one another in such a way that one of the components loses contact with the force sensor;
the evaluation unit comprises at least one further sensor;
the evaluation unit comprises an energy source in the form of a battery; and
the evaluation unit comprises a radio interface.

19. The method as claimed in claim 5, including at least one of the following:
the external display device can indicate to a user whether the actuated second end position was achieved with the last discharge; and
the display device sends at least one of the detected measurement data and data for detecting or not detecting the force increase characteristic of reaching the actuated second end position to an external server.

* * * * *